United States Patent
Pindiprolu et al.

(10) Patent No.: US 9,429,011 B2
(45) Date of Patent: Aug. 30, 2016

(54) METHOD AND APPARATUS FOR IN-SITU FLUID INJECTOR UNIT

(71) Applicant: HALLIBURTON ENERGY SERVICES, INC., Houston, TX (US)

(72) Inventors: Sairam KS Pindiprolu, Mumbai Maharashtra (IN); Bhargav Gajji, Pune Maharashtra (IN); Ganesh Shriniwas Pangu, Maharashtra (IN)

(73) Assignee: Halliburton Energy Services, Inc., Houston, TX (US)

( * ) Notice: Subject to any disclaimer, the term of this patent is extended or adjusted under 35 U.S.C. 154(b) by 321 days.

(21) Appl. No.: 13/941,047

(22) Filed: Jul. 12, 2013

(65) Prior Publication Data

US 2015/0013447 A1    Jan. 15, 2015

Related U.S. Application Data

(63) Continuation-in-part of application No. PCT/US2013/042306, filed on May 22, 2013, which is a continuation-in-part of application No. 13/478,747, filed on May 23, 2012, now abandoned, which is a continuation of application No. 12/869,447, filed on Aug. 26, 2010, now Pat. No. 8,347,693.

(51) Int. Cl.
*E21B 49/00* (2006.01)
*G01N 11/14* (2006.01)

(52) U.S. Cl.
CPC ............. *E21B 49/008* (2013.01); *G01N 11/14* (2013.01)

(58) Field of Classification Search
CPC ............................ E21B 49/008; G01N 11/14
USPC ....... 73/152.39, 54.39, 152.51, 54.26, 54.32, 73/54.33; 166/250.01, 108, 61
See application file for complete search history.

(56) References Cited

U.S. PATENT DOCUMENTS 3,435,666 A    4/1969  Fann
4,096,059 A *  6/1978  Pinkerton ..................... 210/647
(Continued)

FOREIGN PATENT DOCUMENTS

GB           810242          3/1959

OTHER PUBLICATIONS

Riverhawk, "Cantilevered (Single-Ended) Pivot Bearings," Cantilevered Pivot Bearing Characteristics and Applications, 2009, 2 pages, retrieved Aug. 15, 2014, <https://web.archive.org/web/20090201145351/http://flexpivots.com/cantileveredpivotbearings.asp>.

(Continued)

*Primary Examiner* — Michael A Lyons
*Assistant Examiner* — David L Singer
(74) *Attorney, Agent, or Firm* — John W. Wustenberg; Baker Botts L.L.P.

(57) ABSTRACT

Disclosed is a method of testing liquids at a test pressure. A first fluid is placed in a first chamber of a test system. The first fluid is brought to the test pressure. A volume is calculated of a second fluid to inject into the first chamber from a second chamber of the test system via a first portion connecting the first chamber and the second chamber. The first portion includes a fluid interface between the first fluid and the second fluid located in the first portion. The volume of the second fluid is injected into the first chamber, displacing an equivalent volume of fluid into a third chamber of the test system via a second portion connecting the first chamber and the third chamber in fluid communication with each other. The volume of the second fluid in the first chamber is mixed with a remaining volume of the first fluid in the first chamber to create a combination fluid. The combination fluid is tested.

20 Claims, 4 Drawing Sheets

(56) References Cited

U.S. PATENT DOCUMENTS

| | | | |
|---|---|---|---|
| 4,668,911 A | 5/1987 | Mueller | |
| 5,535,619 A | 7/1996 | Brookfield | |
| 5,717,131 A | 2/1998 | Sunde et al. | |
| 5,770,795 A * | 6/1998 | Behar et al. | 73/54.23 |
| 6,564,653 B2 | 5/2003 | Desbiolles | |
| 6,860,137 B2 | 3/2005 | Kitagawa | |
| 6,951,127 B1 | 10/2005 | Bi | |
| 7,128,142 B2 | 10/2006 | Heathman | |
| 7,412,877 B1 * | 8/2008 | Bi | 73/54.28 |
| 7,743,674 B2 | 6/2010 | Boncan | |
| 2004/0224419 A1 * | 11/2004 | Zheng et al. | 436/69 |
| 2006/0070426 A1 | 4/2006 | Pelletier | |
| 2006/0075892 A1 * | 4/2006 | Dorr | 92/5 R |
| 2008/0083268 A1 * | 4/2008 | Hammami et al. | 73/54.01 |
| 2008/0236253 A1 * | 10/2008 | Tehrani et al. | 73/38 |
| 2008/0259335 A1 | 10/2008 | Raghuraman et al. | |
| 2011/0059462 A1 | 3/2011 | Lim et al. | |
| 2011/0295509 A1 * | 12/2011 | Huynh et al. | 702/12 |
| 2014/0352948 A1 * | 12/2014 | Barral et al. | 166/250.01 |

OTHER PUBLICATIONS

International Search Report and Written Opinion issued in related PCT application No. PCT/US2014/045381, mailed Oct. 22, 2014 (8 pages).

International Preliminary Report on Patentability issued in related PCT application No. PCT/US12014/045381, mailed on Jan. 21, 2016 (6 pages).

* cited by examiner

| INITIAL PERCENTAGE OF FLUID A | INITIAL PERCENTAGE OF FLUID B | FINAL PERCENTAGE OF FLUID B | VOLUME OF FLUID B TO BE INJECTED | FLUID B INJECTED |
|---|---|---|---|---|
| 100% | 0% | 25% | 80cc | 80cc |
| 75% | 25% | 50% | 106.66cc | 186.66cc |
| 50% | 50% | 75% | 160cc | 346.66cc |
| 25% | 75% | 100% | 320cc | 666.66cc |
| 0% | 100% | | | |

METHOD AND APPARATUS FOR IN-SITU FLUID INJECTOR UNIT

CROSS REFERENCE TO RELATED APPLICATIONS

This application is a continuation-in-part of International PCT Patent Application No. PCT/US13/042306 filed on May 22, 2013, which is a continuation-in-part of U.S. patent application Ser. No. 13/478,747 filed on May 23, 2012, which is a continuation of U.S. Pat. No. 8,347,693, entitled APPARATUS AND METHODS FOR CONTINUOUS COMPATABILITY TESTING OF SUBTERRANEAN FLUIDS AND THEIR COMPOSITIONS UNDER WELLBORE CONDITIONS, by Pindiprolu, et al., filed Aug. 26, 2010, the entire contents of which are incorporated herein by reference.

BACKGROUND

1. Technical Field

The invention relates to a testing apparatus and a method for conducting tests of compatibility on wellbore fluids and their contaminated mixtures and slurries under specific pressure and temperature conditions and, in particular, an apparatus and method for testing fluid mixtures and slurries for use in subterranean wellbores under simulated wellbore conditions.

2. Background Art

When drilling, completing, and treating subterranean hydrocarbon wells, it is common to inject materials fluid form with complex structures, such as, suspensions, dispersions, emulsions and slurries. These injected materials are present in the wellbore with materials such as water, hydrocarbons, and other materials originating in the subterranean formations. The materials present in the wellbore will be referred to herein as "wellbore fluids" or "wellbore liquids." These substances and their mixtures flow rather than plastically deform. The flow of these fluids and mixtures cannot be characterized by a single value, instead the apparent viscosity and shear stress changes due to other factors such as temperature and pressure and the presence of other materials. Indeed, the materials in some mixtures may be characterized as incompatible. Two fluids are incompatible if undesirable physical and/or chemical interactions occur when the fluids are mixed. Many times incompatibility is characterized by apparent viscosity and shear stress. When apparent viscosity of fluids A and B combined is greater or lesser than apparent viscosity of fluid A as well as apparent viscosity of fluid B, then fluid A and fluid B are said to be incompatible at the tested shear rate.

Cement is placed in wellbore annulus to block or seal off fluid flow, isolate hydrocarbon zones, and provide support for well casings. Wellbores typically are at elevated temperatures and pressures, and contain contaminating fluids and solids. The flow characteristics of various cement mixtures are estimated based on the testing of cement in the presence of a contaminant, such as a fluid spacer, drilling mud, salt water brines or hydrocarbons. In addition, mixtures of spacer fluids and drilling mud are also tested. Other examples, including mixtures of wellbore fluids pumped into the wellbore to carry particulate in suspension to the hydrocarbon bearing formations, are located outside the wellbore.

It is common to determine optimum wellbore liquids and incompatibility of those liquids in a laboratory by running a series of tests of different liquid mixtures under wellbore conditions. Testing various ratios of mixtures of wellbore liquids is done to replicate the changes in the wellbore concentrations of the fluids, either due to contamination with what is pumped downhole or what may exist downhole. These wellbore liquids and mixtures that have variable viscosity are sometimes called "non-Newtonian fluids." Testing a series of samples of actual wellbore mixtures during well treatment is also common. Viscosity, elasticity, shear stress, and consistency are rheological characteristics that need to be measured for a given fluid or mixture.

Known devices used to test fluids for these characteristics include viscometers, rheometers, and consistometers. Testing comprises filling a test chamber with a fluid mixture, bringing the chamber to pressure and temperature test conditions, and then conducting tests of the fluids characteristics. In prior art devices the successive test of different mixture ratios requires emptying and refilling the test chamber with a different mixture to repeat the test. As this process requires pressurization/depressurization and heating/cooling to be done every time the sample is changed, this process consumes a lot of time in preparation of the test for well bore conditions.

SUMMARY OF THE INVENTION

The present invention provides equipment and procedures for successively and accurately testing the compatibility of a series of wellbore fluids, fluid mixtures, and fluid slurries in the presence of contaminants and under pressure and temperature conditions existing in the well.

BRIEF DESCRIPTION OF THE DRAWINGS

The drawings are incorporated into and form a part of the specification to illustrate at least one embodiment and example of the present invention. Together with the written description, the drawings serve to explain the principles of the invention. The drawings are only for the purpose of illustrating at least one preferred example of at least one embodiment of the invention and are not to be construed as limiting the invention to only the illustrated and described example or examples. The various advantages and features of the various embodiments of the present invention will be apparent from a consideration of the drawings in which.

DETAILED DESCRIPTION

The present invention provides an improved testing apparatus and method for successively testing a variety of combinations of fluid and solid based additives for use in subterranean hydrocarbon wells. The present invention's particular applicability is to the testing of various proportional mixtures of drilling mud and fluid spacers, and the testing of various proportional mixtures of drilling mud, fluid spacers, saltwater brines, hydrocarbons, and cement.

The system enables the injection of fluids, including particle laden fluids, at high temperature and high pressure into a parent cell, at high pressure and possibly high temperature wellbore conditions, which requires composition variation of the containing fluid to study the phenomenon of high pressure and possibly high temperature fluid injection on the formation like substances, and/or to characterize of the effect of the injected fluid's ability to perform certain wellbore jobs. The composition variation of the containing fluid is based on the percentage of the different fluids in the current mixture. For example, 10% by volume of fluid A is mixed with 90% by volume of fluid B to make the current fluid in the system of a composition 10-90%. If the parent fluid is A and the injected fluid is B, the system can vary the composition with respect to increase in fluid B volume in the resultant mixture. The system is capable of handling particle laden fluids, like cement, spacer, mud etc., for the purpose of injecting fluids in-situ to another medium or fluid required to study the wellbore phenomenon, which happens during various stages of wellbore operations. Since the main objective of the fluid injection is intended for concentration variation of the fluids in the parent cell, the parent cell should be capable of efficient mixing of the injected fluid with the parent fluid to achieve the compositions required. The system injects the particle laden fluid into the parent cell with parent fluid held at constant pressure. The system accommodates the variation in the fluid volumes due to temperature changes or due to inherent chemical reactions, and maintains the right composition of the parent fluid vs. the injected fluid and pressure in the system. This allows the parent system to measure the properties with variable compositions held constant at high pressure and high temperature condition or measure the properties while the composition is changing.

Figure 1:
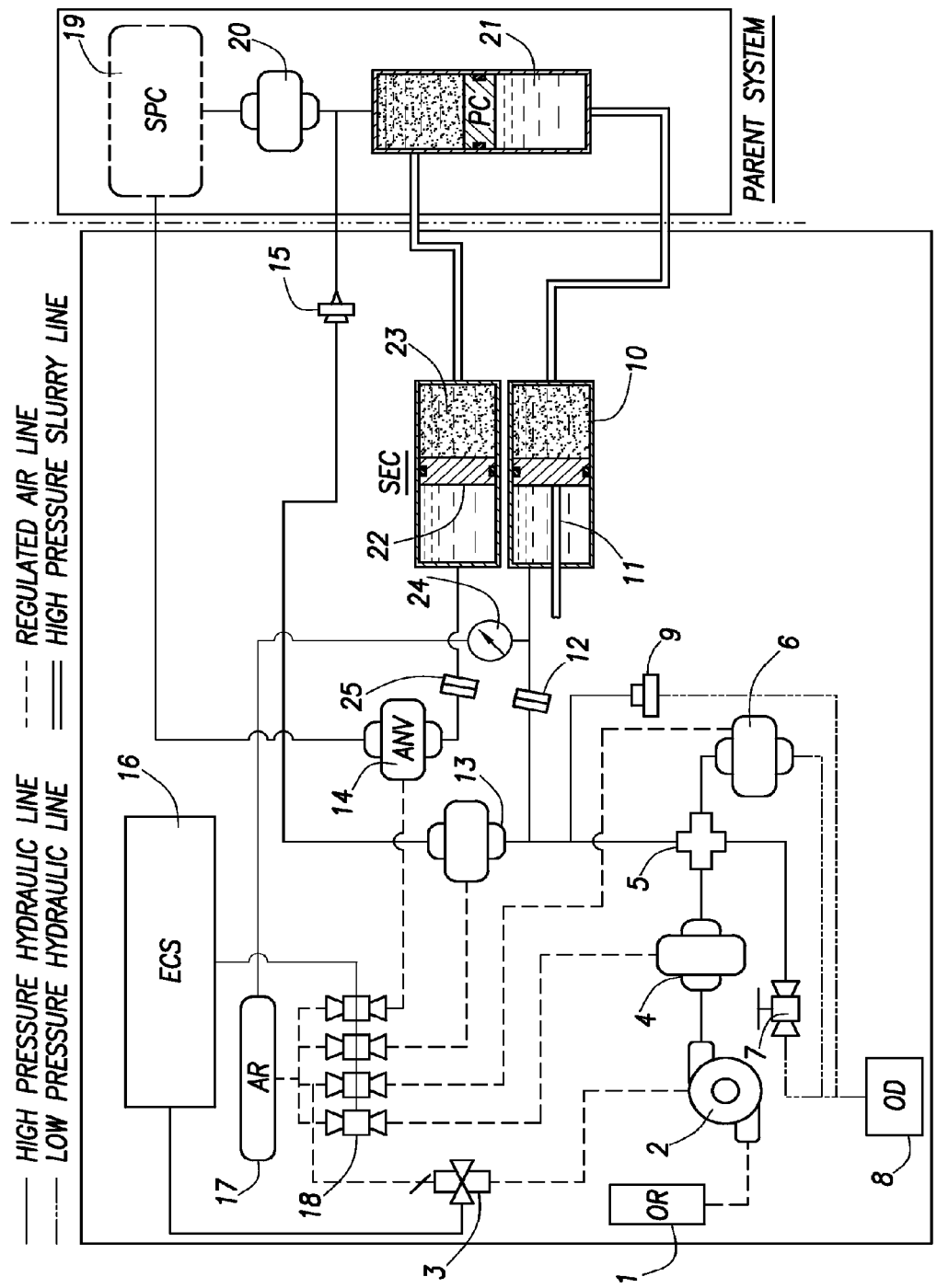
FIG. 1 is a process diagram illustrating the system according to the present invention.

Referring more particularly to the drawings, wherein like reference characters are used throughout the various figures to refer to like or corresponding parts, this is shown in FIG. 1 one embodiment of the system of the present invention. A fluid reservoir 1 is connected to an air operated low flow rated pump 2. The maximum output pressure of the air operated low flow rated pump 2 is controlled by the air pressure inputted to the pump. An electronically operated air intake valve 3 controls the air pressure to the air operated low flow rated pump 2, which in turn controls the hydraulic pressure output from the air operated low flow rated pump 2. The air operated low flow rated pump 2 has a high air to hydraulic pressure ratio and a low volume flow rate. The low volume flow rate enables the injection volume changes to be precise, in the range up to a 100th of 1 cc of volume. The cost of the operation and assembly of the air operated low flow rated pump 2 is economical and easy for maintenance. However, if the ratio of air inlet pressure to the exit hydraulic pressure is high, even though it may help in achieving the injection pressure in less number of strokes, controlling the variation may be difficult. Therefore, a compromise may be considered based on the pressure rating and precision of control for a given assembly.

This high pressure output from the air operated low flow rated pump 2 is connected to a quadruple connection 5 through an air operated needle valve 4. The quadruple connection 5 joins the pump output to connections from an air operated needle valve 6, an emergency needle valve 7, and an accumulator cell 10. A rupture disk 9, rated for maximum operating pressure, is also connected in the line of the accumulator cell 10 to avoid any over pressure beyond rating. The air operated needle valve 6 is operated for the purpose of controlled pressure release and the emergency needle valve 7 is operated for the purpose of sudden pressure release to a discharge location 8 (OD). All of the air operated needle valves 4, 6, 13, and 14 are kept in normally closed condition. During operation, the pump output pressure is connected to the accumulator cell 10 to activate the movement of a piston 11 to start the injection of the particle laden fluid, via a high pressure slurry line, into the bottom most point of a parent cell 21 to vary the parent fluid composition by the displacement method.

The accumulator cell 10 keeps both fluids at a balanced position, under high pressure and high temperature conditions, and provides a measure for the amount of the fluid injected. A high pressure and high temperature cell with the piston 11 and suitable end caps may be assembled together to carry pressurizing fluid on one side and particle laden fluid on the other side. Other considerations include ease of maintenance, provision for heating, monitoring temperatures, and the cost of the equipment. Design alternatives for the accumulator cell 10 are discussed below in reference to FIG. 4.

The parent cell 21 is a pressure vessel designed to be used in controlled temperature and pressure tests up to subterranean hydrocarbon wellbore operating temperatures as high as about 700 degrees Fahrenheit and pressures as high as about 60,000 pounds per square inch. In one embodiment, the parent cell 21 may be similar to, but not limited to, the testing apparatus shown in U.S. Patent Application No. 2012/0048008, which is incorporated herein for all purposes. Parent cell 21 CAN BE A Dynamic filtration cell such as a FANN-90 creating drilling fluid-rock core interactions- or it can be a stirred autoclave conducting electric or other measurements.

A high pressure fluid filter 12 is assembled in the line entering to the accumulator cell 10 to prevent any particles from entering the operating fluid line, in case a sealing failure by the piston 11 causes the particle laden fluid to enter the hydraulic lines of the operating fluid. Another high pressure slurry line at the opposite end relative to the injection input line, preferably at the top most point of the parent cell fluid interface with the pressurizing fluid, of the parent cell 21 is connected to a slurry ejection cell 23.

The slurry ejection cell 23 collects the waste, including the mixture of parent and injected fluids, or the excess fluid, during the injection operation. The slurry ejection cell 23 may contain a floating piston 22 with operating fluid on one side and the particle laden fluid on the other side, and the operating fluid line may be connected to a parent cell pressure control mechanism through an air operated needle valve 14. A high pressure fluid filter 25 is connected before the air operated needle valve 14 to filter particles should the sealing in the slurry ejection cell 23 fail. The air operated needle valve 14 is operated to isolate the pressure in the slurry ejection cell 23 from parent cell pressure control. The slurry ejection cell 23 receives a fluid excess at a high pressure and possibly a high temperature. The slurry ejection cell 23 is a high pressure and high temperature cell. A floating piston arrangement with hydraulic back pressure may be implemented. Even though separate cells may be utilized for the accumulator cell 10 and the slurry ejection cell 23, separate cells may not be necessary, as indicated below in the design alternatives discussed in reference to FIG. 4.

Apart from these hydraulic lines, one more hydraulic line connects the pressure line of the parent cell 21 to the input line for the accumulator cell 10 via an air operated needle valve 13 and a non-return valve 15. This line helps in maintaining the fluid composition of the parent cell 21 during the heating of the accumulator cell 10 and the parent cell 21. For the purpose of monitoring system pressure, a pressure transducer 24 is connected in the input line of the accumulator cell 10.

The system does not use any valves connected in the high pressure slurry line or any slurry pump due to maintenance and performance problems, and choking and malfunctioning problems. Considering the above challenges, no valves or slurry pumps can handle slurries effectively, and keeping hard fluid boundaries may affect the fluid composition variation. A clear description of the fluid injection process is explained in the later sections, in which fluids interfaces are managed dynamically, to provide pressure control, volume compensation, and constant volume composition of the fluid in the parent cell 21.

The parent cell 21 is connected to the system pressure control 19 via an air operated needle valve 20 for the purpose of isolating the pressure of the parent cell 21 from the system pressure control 19. The air operated needle valve 20 may be replaced by a needle valve. A solenoid manifold 18 operates the air operated needle valves 4, 6, 13, and 14. The inlet to the solenoid manifold 18 is connected a high pressure air reservoir 17 for the air supply. The solenoid manifold 18 contains 4 channel outputs connected to the air operated needle valves 4, 6, 13, and 14. Another pneumatic line is connected to the electronically operated air intake valve 3 that controls the air inlet to the air operated low flow rated pump 2.

An electronic control system 16 automates the system. The solenoid manifold 18, which controls the air operated needle valves 4, 6, 13, and 14, requires a digital input, the electronically operated air intake valve 3 requires an analog input, and a pressure transducer requires analog output terminals for the interaction. Apart from these devices, a linear measurement system at the end of the piston 11, like a linear variable differential transformer or other linear measurement systems, requires an analog output terminal for operation. A direct current power supply, as per each device rating, is required for operation. In one embodiment, the electronic control system 16 is a computer controlled data acquisition system, with output terminals to interact with all the devices. An external direct current voltage supply with required voltage output is included in the system.

Heating may be required for the accumulator cell 10 to attain operating temperature for the fluid to be injected. Since a heating system may be operated independently, the heating system does not affect the current mechanical operation of the system. Sometimes it is preferred to heat the mixture in the parent cell 21. Therefore, a parent cell heating control can take care of the mixture heating. The system may compensate for the volume and pressure of the injection fluid during the heating process, as discussed below in reference to FIG. 2.

The accumulator cell 10 may be filled to maximum capacity with a particle laden fluid, or slurry. If the accumulator cell 10 includes a rod, the rod length may be at its maximum. The accumulator cell 10 is deaerated during setup. The piston of the slurry ejection cell 23 may be brought to its extreme end, close to the inlet port for the parent cell 21, so that the slurry ejection cell 23 may receive the maximum fluid during operation. The slurry ejection cell 23 is also deaerated. The accumulator cell 10 and the slurry ejection cell 23 may be filled with the same pressurization fluid. The output from the accumulator cell 10 may be connected at the bottom most point of the parent cell 21 and the inlet to the slurry ejection cell 23 may be connected just below the interface of the pressurization fluid and the system fluid in the parent cell 21.

The fluid from the accumulator cell 10 should not enter the parent cell 21 during testing or pressurization. The fluid from the slurry ejection cell 23 should not enter the parent cell 21 during testing or pressurization. The fluid from the parent cell 21 may enter the accumulator cell 10 because the fluid from the parent cell 21 does not affect the volume composition of the fluid in the parent cell 21, but the volume of fluid injected has to be accounted for during the next operation. In order to account for this, the volume of the fluid that entered from the parent cell 21 into the accumulator cell 10 is recorded based on the position of the piston 11. Fluid interfaces between the fluid in the accumulator cell 10 and fluid in the parent cell 21, and between the fluid in the slurry ejection cell 23 and the fluid in the parent cell 21 should remain intact.

Figure 2:
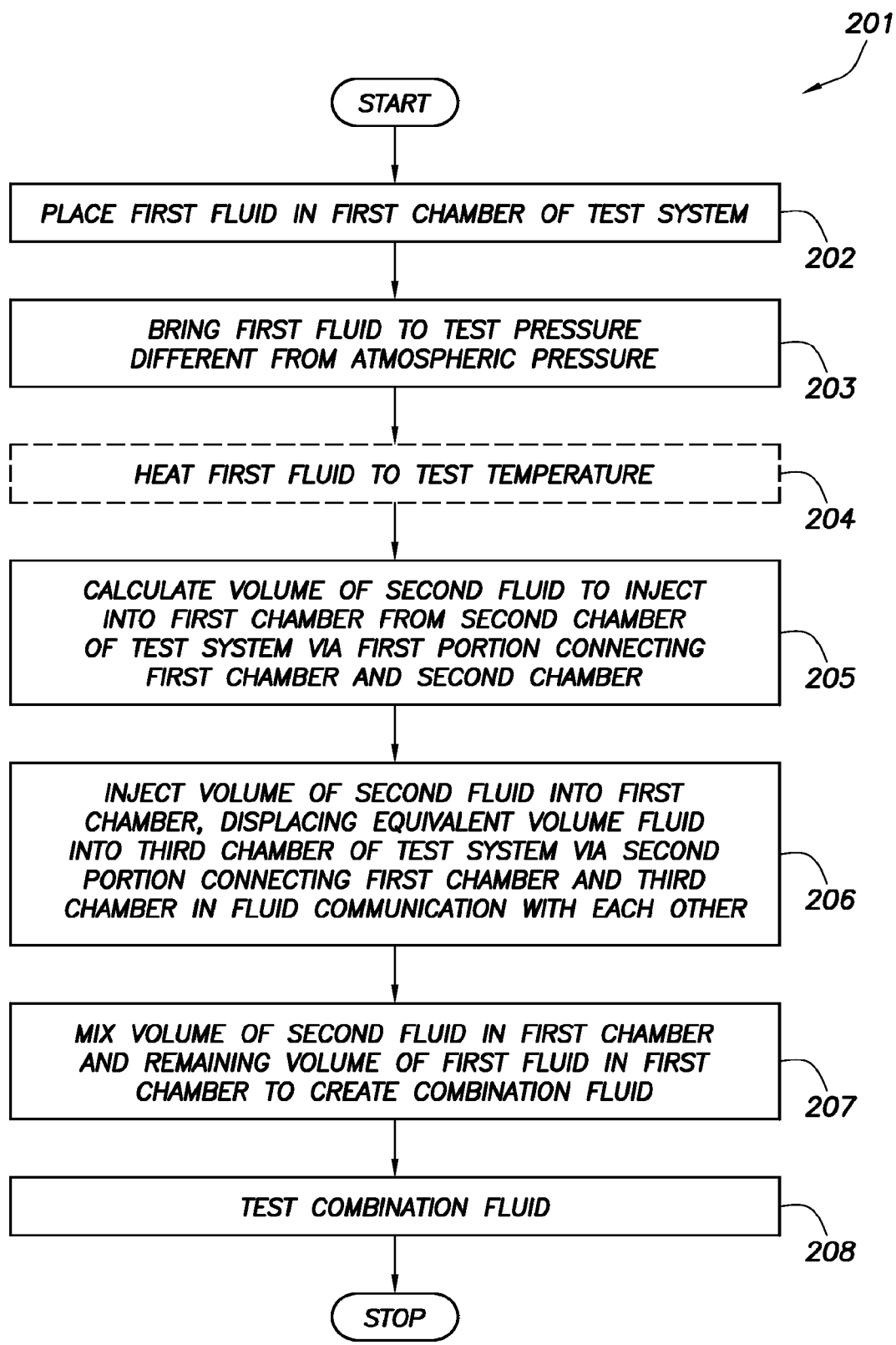
FIG. 2 is a flowchart of a sample method according to the present invention.

Turning now to FIG. 2, a flowchart of a sample method 201 of the present invention is depicted. The system may execute the method 201 to test a combination of fluids at a test pressure, and possibly at a test temperature. The objective of the test could be to capture the characteristics of the resultant fluid after varying the composition of parent cell's fluid or just to inject a fluid at high pressure and high temperature into the parent cell to study various wellbore phenomenon. Although the method 201 focuses on the first scenario; nevertheless the same procedure can be applied to the second scenario with applicable modifications.

In box 202, a first fluid is placed in a first chamber of a test system. For example, a particle laden fluid A is placed in the parent cell 21.

In box 203, a first fluid is brought to a test pressure different from atmospheric pressure. For example, the system pressure control 19 of the parent cell 21 starts the pressurizing pump in the system pressure control 19 to pressurize all of the lines except the lines connected after the air operated needle valve 14 and 20, which are downstream of the slurry ejection cell 23 and the parent cell 21. The air operated needle valves 14 and 20 pressurize the slurry ejection cell 23 and the parent cell 21 simultaneously. In order to pressurize the slurry ejection cell 23, it is not necessary to open the air operated needle valve 14, but pressurizing the slurry ejection cell 23 from the parent cell 21 side may not maintain the fluid interfaces. This starts the pressurization of the parent cell 21, the slurry ejection cell 23 and the accumulator cell 10. During the pressurization, the piston 11 may move because of the compressibility of the injection fluid. This change has to be monitored to record the volume of the fluid that entered from the parent cell 21 into the accumulator cell 10 based on the position of the piston 11. This pressurization continues until the required pressure is achieved. Once the required pressure is achieved, the air operated needle valve 14 is closed to disconnect the slurry ejection cell 23 from the system pressure control 19. In this configuration, the parent cell 21, the accumulator cell 10, and the pressure of the slurry ejection cell 23 are controlled through only one channel connected upstream of the air operated needle valve 20.

In box 204, a first fluid is optionally heated to a test temperature. For example, the air operated needle valve 13 is opened, and heating is started on both the accumulator cell 10 and the parent cell 21. By opening the air operated needle valve 13, the accumulator cell 10 communicates with the system pressure control 19, but the flow is restricted in one direction by the non-return valve 15. This is possible, only when air operate needle valve 20, which is a non-return valve, is open. This provides room for the fluid in the accumulator cell 10 to expand without ejecting fluid into the parent cell 21. At the same time, any pressure changes in the system pressure control 19 will not affect the accumulator cell 10. Once the required temperature is achieved, the air operated needle valves 13 and 20 are closed to isolate the pressure of the parent cell 21 from the system pressure control 19. At this stage, the system is both pressurized and brought to an operating temperature. If further heating is not required, the air operated needle valve 20 is closed to isolate the pressure of the parent cell 21 from the system pressure control 19. At this point, the testing may be conducted on the current fluid in the parent cell 21 or the dosing operation to change the composition of the current fluid in the parent cell 21 can be carried out.

In box 205, the volume is calculated of a second fluid to inject into a first chamber from a second chamber of a test system via a first portion connecting the first chamber and the second chamber. For example, the amount of volume to be injected to vary the current composition to a required composition of fluid in the parent cell 21 is calculated. An initial percentage of the second fluid in the first chamber is subtracted from a goal percentage of the second fluid in the first chamber to create a first preliminary result, the initial percentage of the second fluid in the first chamber is subtracted from 1.0 to create a second preliminary result, the first preliminary result is divided by the second preliminary result to create the third preliminary result, and the third preliminary result is multiplied by a fluid volume capacity of the first chamber to calculate the volume of the second fluid to be injected. Examples of volume calculations are discussed below in reference to FIG. 3.

In box 206, a volume of a second fluid is injected into a first chamber, displacing an equivalent volume of fluid into a third chamber of a test system via a second portion connecting the first chamber and the third chamber in fluid communication with each other. For example, the air operated low flow rated pump 2 starts by opening the electronically operated air intake valve 3. The presumption is that the injection pressure is set by the electronically operated air intake valve 3 to be slightly higher than the operating pressure of the parent cell 21, and the hydraulic lines downstream of the accumulator cell 10 are kept at the injection pressure. The air operated needle valves 4 and 14 open to allow the fluid in the accumulator cell 10 to inject into the parent cell 21, which results in the slurry ejection cell 23 receiving excess fluid, which is fluid that was displaced from the parent cell 21. In order to get controlled injection, a volume measurement system is required for the purpose of the monitoring. The entity to be measured may be the length of a rod of the piston 11. A linear variable differential transformer may be used for the monitoring. In other design alternatives, the measurement system may change based on the entity to be measured, or the technique of measurement of the entity may vary. Design alternatives are discussed below in reference to FIG. 4.

In box 207, a volume of a second fluid in a first chamber is mixed with a remaining volume of a first fluid in the first chamber to create a combination fluid. For example, the parent cell 21 uses an axially rotating shaft actuated by a motor to mix the fluid previously alone in the parent cell 21 with the injected fluid as the injected fluid enters. During the injection process, the parent cell 21 monitors the volume of the fluid injected into the parent cell 21 from the accumulator cell 10 with respect to the change in the position of the piston 11. The position variation is electronically monitored with the help of any linear measurement transducer, like a linear variable differential transformer. Once the corresponding measurement of the piston 11 position is achieved, the air operated needle valves 4 and 14 close to isolate the system from the pressure of the air operated low flow rated pump 2. The air operated low flow rated pump 2 stops to finish the injection of the fluid from the accumulator cell 10.

In box 208, a combination fluid is tested. For example, a viscometer, a rheometer, and/or a consistometer tests the combination fluid, generating the results for the current composition. Other procedures can be performed including testing for electrical, physical chemical and electrochemical and rheological properties. In other scenarios where the fluid injection is only to check the properties of the well bore rock samples or reaction with metal sample, then the fluid injection vs the property changes on these rock/metal compounds will be measured.

Although FIG. 2 depicts the boxes 202-208 occurring in a specific order, the boxes 202-208 may occur in another order. After the testing, the composition may be varied to a higher percentage of the injected fluid, such that the method 201 may be repeated. Once the testing at all the required compositions is completed, the air operated needle valves 14 and 20 open and the system pressure control 19 is set for depressurization. As the pressure reduces to the ambient condition, the system pressure control 19 stops to finish the test.

All the components can be easily disassembled and cleaned. For a quick replacement of the fluids in the slurry ejection cell 23 and the accumulator cell 10, a simple method may be adopted. After the completion of injection, a pneumatic line is connected to the accumulator cell 10 on the slurry side, the piston reaches close to the end cap, and air pressure pushes the piston to the other end for the preparation of filling with injection fluid. After this operation, the injection fluid is filled in the accumulator cell 10 by opening the end cap. After the injection, the slurry ejection cell 23 receives fluid which is accumulated and should be removed. A slurry line is be attached which connects to the drain reservoir, and the slurry ejection cell 23 is pressurized on the pressurization fluid side. This makes the excess fluid in the slurry ejection cell 23 eject out into the slurry line and get deposited into the drain reservoir. Once the slurry accumulated in the slurry ejection cell 23 is completely removed, the pressurization is stopped and the high pressure slurry line is reconnected for another injection operation.

Figure 3:
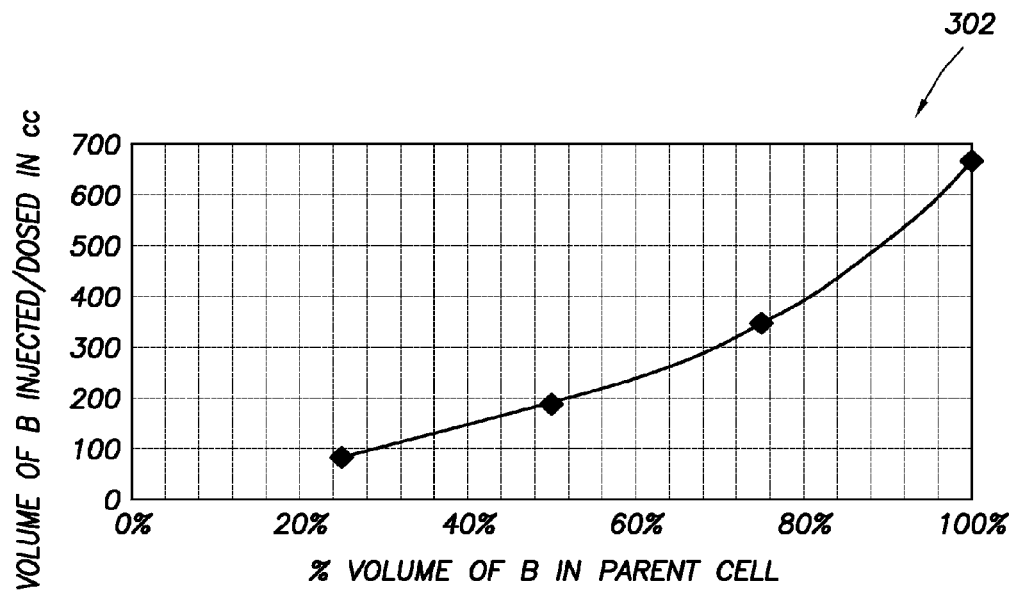
FIG. 3 is a table and a chart illustrating the volume injected to achieve the full range of compositions according to the present invention.

Turning now to FIG. 3, a table 301 and a chart 302 illustrate the volume injected from the accumulator cell 10 to achieve the full range of compositions with increments of 25% in a parent cell 21 with a volume of 320 cc. In order to change composition of a fluid A in the parent cell 21, a volume of fluid B is injected from the accumulator cell 10 into the parent cell 21 and an equal amount of a mixture of fluid A and fluid B is displaced from the parent cell 21 into the slurry ejection cell 23. For the initial volume composition of fluids A and B, the percentage of volume that is fluid B=X, and the percentage of volume that is fluid A=(1−X). For the final composition that needs to be achieved, the percentage of volume that is fluid B=Y, and the percentage of volume that is fluid A=(1−Y). A volume Z of fluid B enters at the bottom of the parent cell 21, and the same amount of volume [a volume Z of the mixture of fluids A and B, with an initial volume composition of (1−X) for fluid A, and X for fluid B] is ejected out from the top of the parent cell 21 to the slurry ejection cell 23. During or after the injection, mixing achieves the final volume composition, resulting in consistency throughout the mixed fluid. The final composition of the mixture of fluids A and B is (1−Y)

for fluid A and Y for fluid B. The value of Z can be calculated in terms of X and Y as follows. The volume of the parent cell 21 is V. Initially, $$V=(1-X)(V)+(X)(V)$$

When the volume Z of fluid B is injected into the parent cell 21, the volume Z of the mixed fluid A and B is ejected out of the parent cell 21 into the slurry ejection cell 23.

$$V=(1-X)(V-Z)+(X)(V-Z)+Z$$

V equates to the final composition of the mixture of fluids A and B.

$$V=(1-Y)(V)+(Y)(V)$$

Based on these two most recent equations, and by equating the volume of the fluid B:

$$(X)(V-Z)+Z=(Y)(V)$$

$$(X)(V)+(1-X)(Z)=(Y)(V)$$

$$(1-X)(Z)=(Y-X)(V)$$

$$Z=(V)(Y-X)/(1-X)$$

The last equation calculates the volume of the fluid B to be injected into the parent cell 21 to vary the composition of the fluids A and B from (1−X) and X to (1−Y) and Y. The volume to be injected depends on V, X, and Y. This calculation provides the basis for the total volume of the fluid B in the accumulator cell 10 to achieve all the compositions to be tested. For example, FIG. 3 depicts the table 301 with composition variations using the increments of 25%. The table 301 indicates the total volume to be injected from the accumulator cell 10 to achieve the full range of compositions based on increments of 25% with the volume of the parent cell 21 at 320 cc. The table indicates that a total of 667 cc is required to achieve all these compositions. The chart 302 presents a representation of the cumulative volume injected with respective to the change in the percentage of the fluid B volume. With the change in the number of compositions and the volume of the parent cell 21, the total volume of the fluid B to be injected changes. Therefore, the volume of the accumulator cell 10 is maintained to contain the required amount of fluid B. Similarly, an equal amount of volume may be assigned to the slurry ejection cell 23 to collect the ejected fluid.

Figure 4:
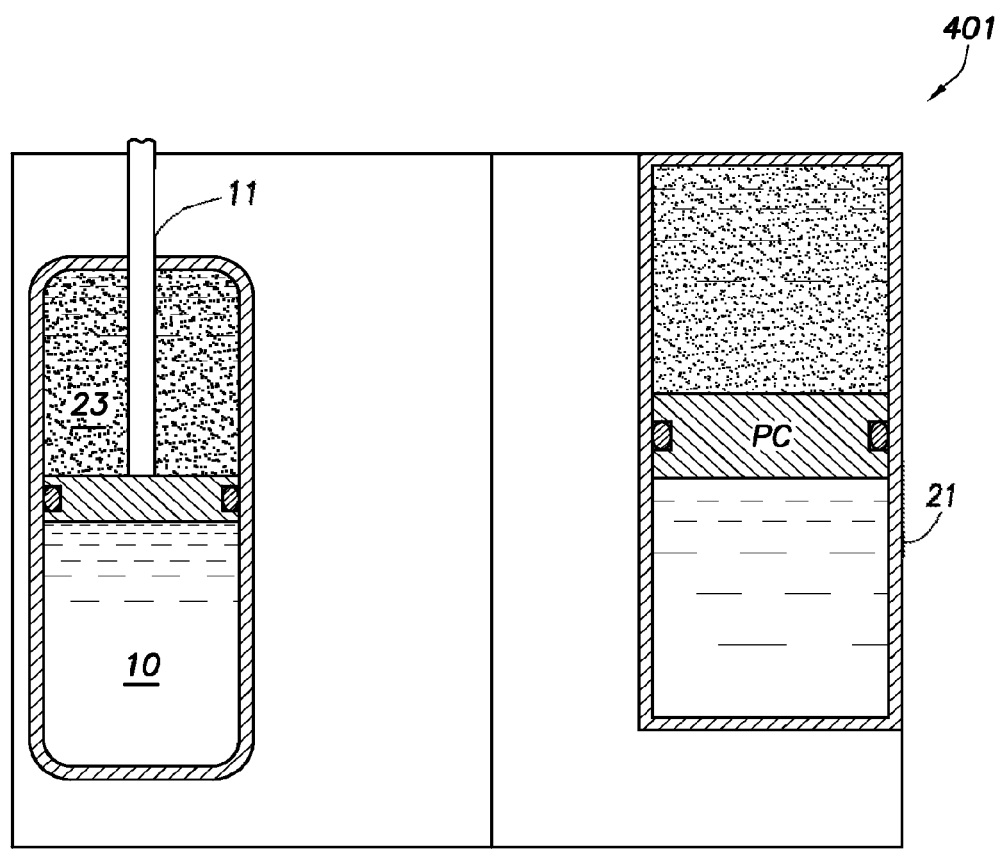
FIG. 4 is a diagram illustrating a design alternative according to the present invention.

Turning now to FIG. 4, a diagram of a design alternative for the accumulator cell 10 is illustrated according to the present invention. Many design alternatives are possible for the accumulator cell 10. The accumulator cell 10 may include a mechanical rod (which is connected to a linear actuator) that actuates the piston 11.

In one design alternative, the accumulator cell 10 may include a permanent magnet placed, assembled, or inserted, on the piston 11, where the measurement entity is the change in the magnetic field of the permanent magnet. The magnetic field of the permanent magnet is sensed by external magnetic field sensors positioned such that the variation in magnetic field strength best represents the position of the piston 11. Advantages of using a permanent magnet include non-contact measurement; the design of the pressure cell can be symmetrical, including the end caps; less room may be required, compared to the rodded piston based measurement; and no high pressure dynamic seals are required, compared to the rodded piston, which may provide the flexibility to increase the pressure rating of the system. A disadvantage of the permanent magnet includes any magnetic particles in the injection fluid possibly settling at the piston surface, causing a variation in the fluid consistency.

Design alternatives for the accumulator cell 10 may be based on the actuation system. The actuation of the rodded piston is by a hydraulic pressure system consisting of positive displacement air operated high ratio air to hydraulic pressure pump. An alternative design that replaces the hydraulic actuation may simplify the system. For example, the hydraulic actuation may be replaced by magnetic actuation, with the rodded piston replaced by a magnetic material piston, and actuation of the magnetic material piston by applying movement to externally coupled magnets, where the motion of the external coupled magnets is controlled by linear actuators. Advantages of magnetic actuation include a simplified unit, with actuation and measurement combined; and smoother operation of the system because the actuation does not produce any fluctuation in pressures as the case in the hydraulic system. Disadvantages of magnetic actuation include the cost of the magnetic coupling and the reliability of the coupling, any change in the injection fluid consistency if the injection fluid contains any magnetic material such as ferrous particles, and the difficulty in locating fluid interfaces after heating and pressurization if the magnetic coupling is rigid during these operations. Therefore, special attention is required to keep the magnetic material piston free to move during these operations and engage the external coupling only after these operations are finished.

Another design alternative for the accumulator cell 10 may be based on the actuation system. The hydraulic actuation may be replaced by linear actuation. A linear actuator may be connected to the end of the mechanical rod of rodded piston in the accumulator cell 10 to control the injection of the fluid. The measurement of the injection volume is calculated by the feedback of the linear actuator. Advantages for linear actuation include a simplified unit, with actuation and measurement combined; and smoother operation of the system because the actuation does not produce any fluctuation in pressures, as is the case in the hydraulic system. Disadvantages for linear actuation include the cost of the linear actuators, and the difficulty in locating fluid interfaces after heating and pressurization if the actuator coupling is rigid during these operations. Therefore, special attention is required to keep the piston 11 free to move during these operations and engage the actuator after these operations.

In a design alternative 401 depicted by the diagram of FIG. 4, the accumulator cell 10 and the slurry ejection cell 23 are separated by the piston 11 and combined in a single cell for operation with the parent cell 21 (PC), and the hydraulic actuation system is replaced by the previously mentioned linear actuator system. Advantages of the combined cell include a small foot print for the system, no pneumatic or hydraulic input is required; and smoother operation of the system as the actuation does not produce any fluctuation in pressures, as is the case in the hydraulic system. Disadvantages of the combined cell include the cost of the linear actuators, the maintenance of the combined cell will increase because the piston sealing system is constantly exposed to the particle laden fluids on both sides, the pressure monitor may be inaccurate because it typically measures the pressure indirectly with the help of a small pressure chamber with a floating piston with clear fluid on the pressure gauge side and particle laden fluid on the other side, depressurization is difficult if any choking happens in the system because it carries particle laden fluid, and the difficulty in locating fluid interfaces after heating and pressurization if the actuator coupling is rigid during these operations. Therefore, special attention is required to keep the piston free to move during these operations and engage the actuator after these operations.

In other design alternatives, just the measurement system can be varied while keeping the rodded piston, such as replacing the linear variable differential transformer with other type of proximity sensors. The choice of proximity sensors depends on the application and accuracy. Examples include ultrasonic proximity sensors and laser based distance measurement devices.

This system, in connection with a Rheometer, can study the compatibility of various fluids at high pressure and high temperature conditions. As there is currently no equipment which can study compatibility of wellbore fluids, such as the interaction of spacer to mud (with in-situ mixing or composition variation) or spacer to cement, this system helps in resolving this challenge. Even though the system is primarily designed for handling wellbore fluids, the system is not limited to handling only wellbore fluids. The system can handle any type of the fluid where it is required to inject one fluid into another fluid at high pressure and possibly temperature. The system tests a wide array of fluids over a wide shear stress range. The system includes all of the advantages of a high temperature high pressure rheometer in addition to the capability to transfer fluids in-situ. The system's simplified design, low maintenance cost, and ease of cleaning enable the generation of significant amount of experimental data during a single test sequence for wellbore fluid admixtures. Even though the main measurement principle mentioned is about viscosity, the system is capable to adapt to other measurements. In the case of metal/rock sample interaction with contaminant fluids or other reactive fluids which may cause variation in the metal/rock property of interest, the current invention can be used as a means to inject fluid at high pressure. Also, the system measurement is not limited by the current system; i.e. measurement of physical, chemical, or electrical, etc. These measurements represent any oil well interactions, like the casing corrosion or formation acidization, etc.

While compositions and methods are described in terms of "comprising," "containing," or "including" various components or steps, the compositions and methods also can "consist essentially of" or "consist of" the various components and steps. As used herein, the words "comprise," "have," "include," and all grammatical variations thereof are each intended to have an open, non-limiting meaning that does not exclude additional elements or steps.

Therefore, the present inventions are well adapted to carry out the objects and attain the ends and advantages mentioned, as well as, those which are inherent therein. While the invention has been depicted, described, and is defined by reference to exemplary embodiments of the inventions, such a reference does not imply a limitation on the inventions, and no such limitation is to be inferred. The inventions are capable of considerable modification, alteration, and equivalents in form and function, as will occur to those ordinarily skilled in the pertinent arts and having the benefit of this disclosure. The depicted and described embodiments of the inventions are exemplary only, and are not exhaustive of the scope of the inventions. Consequently, the inventions are intended to be limited only by the spirit and scope of the appended claims, giving full cognizance to equivalents in all respects.

Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent(s) or other documents that may be incorporated herein by reference, the definitions that are consistent with this specification should be adopted.

The invention claimed is:

1. A method of testing liquids at an elevated test pressure, the method comprising the steps of:
    placing a first fluid in a first chamber of a test system;
    bringing the first fluid to a test pressure different from atmospheric pressure;
    calculating a volume of a second fluid to inject into the first chamber from a second chamber of the test system via a first portion connecting the first chamber and the second chamber, wherein the first portion comprises a fluid interface between the first fluid and the second fluid located in the first portion;
    injecting the volume of the second fluid into the first chamber at a pressure higher than the test pressure, wherein injecting the volume of the second fluid into the first chamber displaces an equivalent volume of fluid into a third chamber of the test system via a second portion connecting the first chamber and the third chamber in fluid communication with each other, wherein the equivalent volume of fluid was present in the first chamber prior to injecting the volume of the second fluid;
    mixing the volume of the second fluid in the first chamber and a remaining volume of the first fluid in the first chamber to create a combination fluid having a volume equal to a total volume of the first fluid that was present in the first chamber prior to injecting the volume of the second fluid; and
    testing the combination fluid.

2. The method according to claim 1, wherein calculating the volume of the second fluid to inject into the first chamber from the second chamber comprises:
    subtracting an initial percentage of the second fluid in the first chamber from a goal percentage of the second fluid in the first chamber to create a first preliminary result;
    subtracting the initial percentage of the second fluid in the first chamber from 100% to create a second preliminary result;
    dividing the first preliminary result by the second preliminary result to create the third preliminary result; and
    multiplying the third preliminary result by a fluid volume capacity of the first chamber to calculate the volume of the second fluid to inject into the first chamber from the second chamber.

3. The method according to claim 1, wherein at least one of the first fluid comprises a first particle laden fluid and the second fluid comprises a second particle laden fluid.

4. The method according to claim 1, wherein testing the combination fluid comprises determining at least one of an apparent viscosity, consistency and rheology of the combination fluid at the test pressure.

5. The method according to claim 1, wherein testing the combination fluid comprises determining at least one of the electrical, physical, chemical, and electrochemical properties of the combination fluid at the test pressure.

6. The method according to claim 1, wherein testing the combination fluid comprises determining reaction solid materials of the combination fluid at the test pressure.

7. The method according to claim 4, wherein determining the apparent viscosity of the combination fluid at the test pressure comprises determining the apparent viscosity of the combination fluid at the test pressure while maintaining the fluid interface in the first portion.

8. The method according to claim 1, additionally comprising the step of heating the first fluid to a test temperature.

9. The method according to claim 8, wherein the testing step is performed at the test temperature.

10. A fluid testing apparatus, comprising:
a first chamber comprising a testing device that tests a first fluid in the first chamber;
a second chamber comprising an injection mechanism that injects a second fluid in the second chamber into the first chamber;
a third chamber;
a pressure control system that brings the first fluid in the first chamber to a test pressure;
a first portion separating the first chamber and the second chamber, forming a first high pressure line connecting the first chamber and the second chamber, and enabling a fluid interface between the first fluid and the second fluid located in the first portion;
a control system to calculate a volume of the second fluid to inject into the first chamber from the second chamber;
a second portion separating the first chamber and the third chamber, and forming a second high pressure line connecting the first chamber and the third chamber in fluid communication with each other, wherein injecting the volume of the second fluid into the first chamber at a higher pressure than the test pressure displaces an equivalent volume of fluid into the third chamber via the second portion, wherein the equivalent volume of fluid was present in the first chamber prior to injecting the volume of the second fluid; and
a mixing device to mix the volume of the second fluid in the first chamber and a remaining volume of the first fluid in the first chamber to create a combination fluid in the first chamber, the combination fluid having a volume equal to a total volume of the first fluid that was present in the first chamber prior to injecting the volume of the second fluid;
wherein the testing device tests the combination fluid.

11. The fluid testing apparatus according to claim 10, wherein the testing device determines at least one of an apparent viscosity and a rheology of the combination fluid at one of the test pressure and temperature while maintaining the fluid interface in the first high pressure line, and wherein the testing device comprises one of a viscometer, a rheometer, and a consistometer.

12. The fluid testing apparatus according to claim 10, wherein the injection mechanism comprises a piston actuated by hydraulic fluid.

13. The fluid testing apparatus according to claim 10, wherein the injection mechanism comprises a piston actuated by a magnet.

14. The fluid testing apparatus according to claim 10, wherein the injection mechanism comprises a piston actuated by a mechanical rod with one of a linear actuator and rotary actuator.

15. The fluid testing apparatus according to claim 10, wherein the injection mechanism comprises a piston that separates the second chamber from the third chamber.

16. The fluid testing apparatus according to claim 10, wherein at least one of the first and second fluids comprises a particle laden fluid.

17. The fluid testing apparatus according to claim 10, wherein the control system calculating the volume of the second fluid to inject into the first chamber from the second chamber comprises:
subtracting an initial percentage of the second fluid in the first chamber from a goal percentage of the second fluid in the first chamber to create a first preliminary result;
subtracting an initial percentage of the second fluid in the first chamber from 100% to create a second preliminary result;
dividing the first preliminary result by the second preliminary result to create the third preliminary result; and
multiplying the third preliminary result by a fluid volume capacity of the first chamber to calculate the volume of the second fluid to inject into the first chamber from the second chamber.

18. The fluid testing apparatus according to claim 10, wherein the third chamber comprises a piston that enables regulation of pressure in the first chamber, the second chamber, and the third chamber.

19. The fluid testing apparatus according to claim 10, wherein the mixing device comprise an axially rotating shaft actuated by at least one of a motor and a magnetic stirrer.

20. The fluid testing apparatus according to claim 10, additionally comprising a heating system that heats the first fluid in the first chamber.

* * * * *